United States Patent
Okura et al.

(10) Patent No.: US 11,540,995 B2
(45) Date of Patent: Jan. 3, 2023

(54) EYE-MAKEUP COSMETIC COMPOSITION

(71) Applicant: LVMH RECHERCHE, Saint-Jean de Braye (FR)

(72) Inventors: Koji Okura, Tokyo (JP); Hideshi Gohara, Tokyo (JP); Takayoshi Sakoda, Kanagawa (JP); Sabine Vic, Semoy (FR)

(73) Assignee: LVMH RECHERCHE, Saint Jean de Braye (FR)

( * ) Notice: Subject to any disclaimer, the term of this patent is extended or adjusted under 35 U.S.C. 154(b) by 0 days.

(21) Appl. No.: 15/302,401

(22) PCT Filed: Apr. 9, 2014

(86) PCT No.: PCT/EP2014/057184
§ 371 (c)(1),
(2) Date: Oct. 6, 2016

(87) PCT Pub. No.: WO2015/154804
PCT Pub. Date: Oct. 15, 2015

(65) Prior Publication Data
US 2017/0027844 A1 Feb. 2, 2017

(51) Int. Cl.
| | |
|---|---|
| *A61Q 1/10* | (2006.01) |
| *A61K 8/81* | (2006.01) |
| *A61K 8/73* | (2006.01) |
| *A41G 5/02* | (2006.01) |
| *A61K 8/02* | (2006.01) |
| *A61K 8/19* | (2006.01) |

(52) U.S. Cl.
CPC .............. *A61K 8/8152* (2013.01); *A41G 5/02* (2013.01); *A61K 8/0216* (2013.01); *A61K 8/19* (2013.01); *A61K 8/731* (2013.01); *A61K 8/735* (2013.01); *A61K 8/737* (2013.01); *A61K 8/8182* (2013.01); *A61Q 1/10* (2013.01); *A61K 2800/413* (2013.01); *A61K 2800/43* (2013.01); *A61K 2800/594* (2013.01)

(58) Field of Classification Search
CPC .......... A41G 5/02; A61K 8/0216; A61K 8/19; A61K 8/731; A61K 8/735; A61K 8/737; A61K 8/8152; A61K 8/8182; A61K 2800/413; A61K 2800/43; A61K 2800/594; A61Q 1/10
See application file for complete search history.

(56) References Cited

U.S. PATENT DOCUMENTS

| | | | |
|---|---|---|---|
| 2002/0168335 A1 | 11/2002 | Collin | |
| 2003/0232030 A1 | 12/2003 | Lu et al. | |
| 2004/0047884 A1* | 3/2004 | Bernard | A61K 8/8111 424/401 |
| 2004/0126345 A1 | 7/2004 | McNamara | |
| 2012/0156271 A1* | 6/2012 | Matsuzawa | A61K 8/03 424/401 |
| 2012/0263662 A1* | 10/2012 | Iimura | A61K 8/891 424/59 |

FOREIGN PATENT DOCUMENTS

| | | |
|---|---|---|
| EP | 0266921 | 10/1987 |
| EP | 2168569 | 3/2010 |
| JP | 2006297038 | 11/2006 |
| JP | 2009040718 | 2/2009 |
| WO | 2012087510 | 6/2012 |

OTHER PUBLICATIONS

Daitosol 5500GM Sep. 26, 2013.*
International Search Report issued in International Application No. PCT/EP2014/057184 dated Dec. 1, 2015 (5 pages).
"Daitosol"; Daito Kasei; XP002680344, Oct. 2007, pp. 1-6, URL:http://www.daitokasei.com/img/e%20chemical/DAITOSOL%20BRO.pdf, retrieved 2012.
"Daitosol"; Daito Kasei Kogyo Co., Ltd; XP002680344, Oct. 2014, pp. 1-14, URL:http://www.daitokasei.com/english/products/DAITOSOLBROCHURE2014.10.10.pdf, retrieved 2014.
P J Flory et al.: "References and Notes" Journal of American Chemical Society, Jan. 1973, pp. 29-2035, http://pubs.acs.org/doi/abs/10.1021/ma60066a018, retrieved 2014.

* cited by examiner

*Primary Examiner* — Jyothsna A Venkat
(74) *Attorney, Agent, or Firm* — MH2 Technology Law Group, LLP

(57) ABSTRACT

The present invention relates to a colored cosmetic composition for making up eyes, in particular eyelids. One of the aspects of the present invention is a colored cosmetic composition for making up eyes, in particular to eyelids, comprising: (i) at least one polymer which has a Tg of −30° C. or less; (ii) at least one hydrophilic thickener; (iii) at least one pigment; and (iv) water. The cosmetic composition according to the present invention can provide a good feeling during use and appropriate adhesiveness to fake eyelashes, and is stable over time.

15 Claims, No Drawings

EYE-MAKEUP COSMETIC COMPOSITION

TECHNICAL FIELD

The present invention relates to a colored cosmetic composition for making up eyes, in particular eyelids, as well as a use of the colored cosmetic composition, and a cosmetic process using the colored cosmetic composition.

BACKGROUND ART

Cosmetic products such as eye shadows and eye liners have been used for making up eyes, in particular eyelids. For example, eyelids with makeup by an eyeliner, which typically has black color, can make the shape of eyes clear, and can make the appearance of eyes larger.

Fake eyelashes are also commonly used for cosmetic treatments for the eyes by attaching the fake eyelashes to the eyelids. In general, fake eyelashes are attached to the eyelids with an adhesive. For example, a user of fake eyelashes applies an adhesive to the base of the fake eyelashes, and adheres the base of the fake eyelashes to the eyelids. Alternatively, an adhesive is applied beforehand to the eyelids, in particular, the edges of the eyelids, and fake eyelashes are attached by a user to the eyelids on which the adhesive has been applied, as disclosed in JP-A-2006-297038.

As eye-makeup cosmetic products and adhesives used for adhering fake eyelashes to eyelids, a variety of cosmetic compositions are known, and have been marketed. In addition, there are some cosmetic products which can be used as both an eyeliner and an adhesive for fake eyelashes.

The eyelids are sensitive portions on the face. Therefore, some conventional eye-makeup cosmetic compositions and adhesives for fake eyelashes tend to impart an uncomfortable feeling during use such as irritation to the eyelids. In addition, conventional adhesives for fake eyelashes are often of a low-grade quality as compared to the adhesives used in cosmetic products which are more directly used for the skin.

Further, some conventional eye-makeup cosmetic compositions tend to provide poor or excessive adhesiveness, and therefore, it is sometimes difficult for them to provide long term makeup effects for eyes, or to be removed from eyelids by a cleansing product when to be removed. Some conventional adhesives for fake eyelashes also tend to exhibit poor adhesiveness which is insufficient to fix the fake eyelashes on the eyelids, in particular, the edges thereof, for a long period of time or excessive adhesiveness which makes it difficult to remove the fake eyelashes when removing make up including the fake eyelashes from the face, in particular, around the eyes.

Furthermore, some conventional eye-makeup cosmetic compositions and adhesives for fake eyelashes are unstable over time such that they cause substantial phase separation. Therefore, there is a need to improve the stability over time of conventional eye-makeup cosmetic compositions and adhesives for fake eyelashes.

DISCLOSURE OF THE INVENTION

An objective of the present invention is to provide a cosmetic composition for making up eyes, in particular eyelids, which can impart a good feeling during use, and appropriate adhesiveness to the eyelids and/or fake eyelashes, and is stable over time.

The objective of the present invention can be attained by a colored cosmetic composition for making up eyes, in particular eyelids, comprising:

(i) at least one polymer which has a Tg (glass transition temperature) of −30° C. or less;
(ii) at least one hydrophilic thickener;
(iii) at least one pigment; and
(iv) water.

It is preferable that the Tg of the polymer used in the present invention be −40° C. or less, more preferably −50° C. or less, and even more preferably −60° C. or less.

It is preferable that the (i) polymer be an adhesive polymer.

The (i) polymer may be formed by at least one monomer selected from the group consisting of $C_{1-6}$ alkyl (meth)acrylates, $C_{1-6}$ hydroxyalkyl (meth)acrylates, $C_{1-6}$ alkoxy $C_{1-6}$ alkyl (meth)acrylates, polyoxyalkylene (meth)acrylates, $C_{1-6}$ alkylpolyoxyalkylene (meth)acrylates, $C_{8-22}$ alkyl (meth)acrylates, olefins, dienes, styrene, vinyl acetate, vinyl chloride, vinylidene chloride, vinylpyrrolidone, (meth)acrylonitrile, (meth)acrylamide, (meth)acrylic acid, and a mixture thereof.

It is preferable that the (i) polymer be selected from the group consisting of acrylates copolymers, acrylates/ethylhexyl acrylate copolymers, and styrene/acrylates copolymers.

The (i) polymer may be in the form of particles.

It is preferable that the average particle size of the (i) polymer be from 100 to 300 nm, more preferably from 120 to 250 nm, and even more preferably from 140 to 200 nm.

The particles of the (i) polymer may be dispersed in the (iv) water.

The amount of the (i) polymer may be 10% by weight or more, preferably 20% by weight or more, and more preferably 30% by weight or more, relative to the total weight of the composition.

The (ii) hydrophilic thickener may be selected from natural polymers, modified natural polymers, and synthetic polymers.

It is preferable that the (ii) hydrophilic thickener be selected from the group consisting of polysaccharides such as xanthan gum, cellulose derivatives such as hydroxyethylcellulose, acrylate (co)polymers except for the (i) polymer, and a mixture thereof.

The amount of the (ii) hydrophilic thickener may be 0.01% by weight or more, preferably 0.1% by weight or more, and more preferably 0.5% by weight or more, relative to the total weight of the composition.

The amount of the (iii) pigment may be 0.01% by weight or more, preferably 0.1% by weight or more, and more preferably 1% by weight or more, relative to the total weight of the composition.

The present invention also relates to the use of a colored cosmetic composition comprising:

(i) at least one polymer which has a Tg of −30° C. or less;
(ii) at least one hydrophilic thickener;
(iii) at least one pigment; and
(iv) water, for making up eyes, in particular eyelids.

The present invention also relates to a cosmetic process comprising:

(1) applying the colored cosmetic composition according to the present invention as above to eyelids; and
(2) adhering fake eyelashes to the eyelids, or (1) applying the colored cosmetic composition according to the present invention as above to fake eyelashes; and
(2) adhering the fake eyelashes to eyelids.

BEST MODE FOR CARRYING OUT THE INVENTION

The inventors performed diligent research and found that a composition including (i) at least one polymer which has a Tg of −30° C. or less; (ii) at least one hydrophilic thickener; (iii) at least one pigment; and (iv) water can impart a good feeling during use when being applied onto eyelids and/or when adhering fake eyelashes to eyelids, in particular, the edges thereof, as well as appropriate adhesiveness to eyelids and/or fake eyelashes such that it can provide eye makeup effects for a long period of time and/or can fix the fake eyelashes on the eyelids, in particular, the edges thereof, for a long period of time, while the eye-makeup and/or fake eyelashes can be removed, when necessary to be removed, with a comfortable feeling of removal from the eyelids. Furthermore, the inventors also discovered that the composition including the above ingredients (i) to (iv) is stable over time.

Thus, the composition according to the present invention is characterized by being used for making up eyes, in particular eyelids, and by including:

(i) at least one polymer which has a Tg of −30° C. or less;
(ii) at least one hydrophilic thickener;
(iii) at least one pigment; and
(iv) water.

Since the composition according to the present invention includes (iii) at least one pigment, it is colored. The colored composition according to the present invention is a cosmetic composition for use in making up eyes, in particular eyelids, preferably the edges of the eyelids.

The colored cosmetic composition according to the present invention will be described below in a detailed manner.

Polymer

The composition according to the present invention comprises at least one polymer which has a Tg of −30° C. or less. Two or more polymers may be used in combination. Thus, a single type of polymer or a combination of different types of polymers may be used. The polymer according to the present invention is preferably a thermoplastic polymer.

The Tg (glass transition temperature) is a well-known property in the art, and can be measured by any conventional means such as TMA (Thermo Mechanical Analysis) and DSC (Differential Scanning calorimetry).

It is preferable that the Tg of the polymer used in the present invention be −40° C. or less, more preferably −50° C. or less, and even more preferably −60° C. or less. Since the polymer used in the present invention has a low Tg, it can exhibit sufficient adhesiveness, even under cold environments such as those in winter.

It is preferable that the polymer used in the present invention be an adhesive polymer.

The polymer used in the present invention may be a homopolymer derived from a single type of monomer or a copolymer derived from two or more types of monomers. It is preferable that the polymer used in the present invention be a copolymer. If the polymer used in the present invention is a copolymer, it can be a random copolymer or a block copolymer. The monomers for the polymer used in the present invention are not limited.

The polymer used in the present invention may be formed by at least one monomer selected from the group consisting of $C_{1-6}$ alkyl (meth)acrylates, $C_{1-6}$ hydroxyalkyl (meth)acrylates, $C_{1-6}$ alkoxy $C_{1-6}$ alkyl (meth)acrylates, polyoxyalkylene (meth)acrylates, $C_{1-5}$ alkylpolyoxyalkylene (meth)acrylates, $C_{8-22}$ alkyl (meth)acrylates, olefins, dienes, styrene, vinyl acetate, vinyl chloride, vinylidene chloride, vinylpyrrolidone, (meth)acrylonitrile, (meth)acrylamide, (meth)acrylic acid, and a mixture thereof.

$C_{1-6}$ alkyl (meth)acrylates can be represented by the formula: $CH_2=CH-COOR^1$ or $CH_2=C(CH_3)-COOR^1$ wherein R' denotes a $C_{1-6}$ linear alkyl group such as a methyl group, an ethyl group, an n-propyl group and an n-butyl group, a $C_{3-6}$ branched alkyl such as an i-propyl group and an i-butyl group, or a $C_{3-6}$ cyclic alkyl group such as a cyclobutyl group, a cyclopentyl group, or a cyclohexyl group.

For example, methyl(meth)acrylate, ethyl(meth)acrylate, propyl(meth)acrylate, butyl(meth)acrylate, isobutyl(meth)acrylate, pentyl(meth)acrylate, and hexyl(meth)acrylate may be mentioned.

$C_{1-6}$ hydroxyalkyl (meth)acrylates can be represented by the formula: $CH_2=CH-COOR^2$ or $CH_2=C(CH_3)-COOR^2$ wherein $R^2$ denotes a $C_{1-6}$ linear hydroxyl alkyl group such as $-CH_2-OH$, $-CH_2CH_2OH$, and $CH_2CH_2CH_2OH$, a $C_{3-6}$ branched hydroxyalkyl such as $-CH(CH_2OH)CH_3$ and $-CH2-CH(CH_2OH)CH_3$, or a $C_{3-6}$ cyclic hydroxyalkyl group such as a hydroxycyclobutyl group, a hydroxycyclopentyl group, or a hydroxycyclohexyl group.

For example, 2-hydroxyethyl(meth)acrylate may be mentioned.

$C_{1-6}$ alkoxy $C_{1-6}$ alkyl (meth)acrylates can be represented by the formula: $CH_2=CH-COOR^3$ or $CH_2=C(CH_3)-COOR^3$ wherein $R^3$ denotes a $C_{1-6}$ alkoxy $C_{1-6}$ linear alkyl group such as a methoxymethyl group, a methoxyethyl group, an ethoxymethyl group, and an ethoxyethyl group, a $C_{1-6}$ alkoxy $C_{3-6}$ branched hydroxylalkyl such as a methoxyisobutyl group and an ethoxyisobutylgroup, or a $C_{1-6}$ alkoxy $C_{3-6}$ cyclic alkyl group such as a methoxycyclobutyl group, a methoxycyclopentyl group, or a methoxycyclohexyl group.

For example, 2-methoxyethyl(meth)acrylate may be mentioned.

Polyoxyalkylene (meth)acrylates can be represented by the formula: $CH_2=CH-COOR^4$ or $CH_2=C(CH_3)-COOR^4$ wherein $R^4$ denotes an -AO—H group where AO denotes an alkyleneoxide chain such as polyethyleneoxide, polypropyleneoxide, polybutyleneoxide, and a mixture thereof. The polyalkyleneoxide chain may include 2-30 units of alkyleneoxide, for example, 5-30 ethyleneoxides.

For example, polyethyleneglycol (meth)acrylate may be mentioned.

$C_{1-6}$ alkylpolyoxyalkylene (meth)acrylates can be represented by the formula: $CH_2=CH-COOR^5$ or $CH_2=C(CH_3)-COOR^5$ wherein $R^5$ denotes an -AO—$C_{1-6}$ alkyl group where AO denotes an alkyleneoxide chain such as polyethyleneoxide, polypropyleneoxide, polybutyleneoxide, and a mixture thereof. The polyalkyleneoxide chain may include 2-30 units of alkyleneoxide, for example, 5-30 ethyleneoxides.

For example, polyethyleneglycol methyl ether (meth)acrylate, and polyethyleneglycol ethyl ether (meth)acrylate may be mentioned.

$C_{8-22}$ alkyl (meth)acrylates can be represented by the formula: $CH_2=CH-COOR^6$ or $CH_2=C(CH_3)-COOR^6$ wherein $R^6$ denotes a $C_{8-22}$ linear alkyl group such as an octyl group, a lauryl group, and a stearyl group, a $C_{8-22}$ branched alkyl such as a 2-ethylhexyl group, or a $C_{8-22}$ cyclic alkyl group such as a cyclooctyl group.

For example, octyl(meth)acrylate, 2-ethylhexyl(meth)acrylate, lauryl(meth)acrylate, and stearyl(meth)acrylate may be mentioned. 2-ethylhexyl(meth)acrylate is preferable, and 2-ethylhexyl acrylate is more preferable.

Olefins may be selected from the group consisting of ethylene, propylene, butene, pentene, hexene, and fluorinated olefins such as tetrafluoroethylene and hexafluoropropylene.

Dienes may be selected from the group consisting of butadiene, isoprene, and halogenated dienes such as chloroprene.

The (meth)acrylic acid may be in the form of a salt, for example, with a metal such as a sodium and potassium, or with an ammonium ion.

At least one additional monomer such as maleic acid, maleic anhydride, maleate, fumaric acid, fumalate, crotonic acid, itaconic acid, acrylamidepropane sulfonic acid, vinylbenzoic acid, and vinylpyridine, may also be used.

The polymer used in the present invention may be a linear or branched (co)polymer, and preferably is a linear (co)polymer.

The polymer used in the present invention can be prepared using the (co)polymerizing monomers for the polymer, preferably those as mentioned above. For example, the (co)polymerization can be performed by conventional free-radical polymerization in a solvent or a dispersant such as water, alcohol (ethanol, isopropanol, or the like), a hydrocarbon (isododecane or the like), ethyl acetate, butyl acetate, and a mixture thereof. For example, a solvent or dispersant in a reactor is heated to an appropriately elevated temperature such as 60-120° C.; appropriately selected monomers are added to the solvent or dispersant to form a solution or dispersion, followed by adding at least one polymerization initiator such as an azo compound (AIBN or the like), and an organic peroxide (di-tert-butylperoxide or the like) to the solution or dispersion; and the solution or dispersion is heated for a certain period of time such as 3 to 12 hours allowing the monomers to react to form the (co)polymer. The obtained (co)polymer can be collected from the solution or dispersion by evaporation, filtration, and the like.

It is preferable that the polymer used in the present invention be selected from the group consisting of acrylates copolymers, acrylates/ethylhexyl acrylate copolymers, and styrene/acrylates copolymers (INCI name). The term "acrylates" here means at least one monomer selected from simple (meth)acrylates, such as $C_{1-6}$ alkyl (meth)acrylates, and (meth)acrylic acids.

It is more preferable that the polymer used in the present invention be selected from acrylates copolymers and acrylates/ethylhexyl acrylate copolymers. It is even more preferable that the polymer used in the present invention be selected from acrylates/ethylhexyl acrylate copolymers.

The acrylates/ethylhexyl acrylate copolymers can be formed, for example, using 30 to 70% by weight, preferably 40 to 60% by weight, of 2-ethylhexyl acrylate, and 30 to 70% by weight, preferably 40 to 60% by weight, of at least one monomer selected from $C_{1-6}$ alkyl (meth)acrylates and (meth)acrylic acids, preferably methyl (meth)acrylate, ethyl (meth)acrylate and (meth)acrylic acid, more preferably (meth)acrylic acid, and even more preferably methacrylic acid.

It is preferable that the polymer used in the present invention not be water-soluble, but water-dispersible.

The polymer used in the present invention may be in the form of particles. It is preferable that the average particle size of the polymer be from 100 to 300 nm, more preferably from 120 to 250 nm, and even more preferably from 140 to 200 nm. The term "average particle size" here means a volume-average (median) particle size which can be determined by, for example, the measurement of laser-diffraction/diffusion of the particles.

The particles of the polymer used in the present invention may be dispersed in a liquid medium, in particular, a hydrophilic liquid medium such as water; lower alcohol such as $C_{1-6}$ alcohol; glycol such as ethyleneglycol, propyleneglycol, and butyleneglycol; glycerol; and a mixture thereof. It is preferable that the particles of the polymer used in the present invention be dispersed in water.

It is preferable that the polymer used in the present invention have a film-forming property.

The polymer suitable for the present invention is available from the market. For example, it is possible to use, as the (adhesive) polymer for the present invention, DAITOSOL 5500GM® (acrylates/ethylhexyl acrylate copolymer) marketed by DAITO KASEI KOGYO Co., Ltd. in Japan. DAITOSOL 5500GM® includes acrylates/ethylhexyl acrylate copolymer with a Tg of −67° C. dispersed in water with a solid content of 55% by weight (in the form of an aqueous dispersion).

It is preferable that the amount of polymer(s) in the composition according to the present invention be 10% by weight or more, more preferably 20% by weight or more, and even more preferably 30% by weight or more, relative to the total weight of the composition.

According to one embodiment of the present invention, the amount of polymer(s) used in the present invention may range from 10 to 80% by weight, preferably from 20 to 70% by weight, and more preferably from 30 to 60% by weight, based on the total weight of the composition according to the present invention.

Hydrophilic Thickener

The composition according to the present invention comprises at least one hydrophilic thickener. Two or more hydrophilic thickeners may be used in combination. Thus, a single type of hydrophilic thickener or a combination of different types of hydrophilic thickeners may be used. The thickener used in the present invention is hydrophilic, and therefore, it can increase the viscosity of water or an aqueous solution. It is preferable that the hydrophilic thickener have no hydrophobic chain such as a $C_{8-30}$ hydrocarbon chain, in particular, alkyl chain.

Due to the presence of the hydrophilic thickener, the composition according to the present invention can have superior stability over time such that it can maintain a homogeneous phase without a substantial phase separation of the composition over a long period of time such as one month.

Any hydrophilic thickener can be used in the present invention as long as it does not impair the stability over time of the composition according to the present invention.

For example, it is possible to use any inorganic hydrophilic thickeners, for example, kaolin; silica; bentonite and derivatives thereof such as Quaternium-18 bentonite, Quaternium-90 bentonite, and stearalkonium bentonite; hectorite and derivatives thereof such as Quaternium-18 hectorite, stearalkonium hectorite, and disteardimonium hectorite; magnesium aluminum silicate; aluminum iron calcium magnesium zirconium silicate; tromethamine magnesium aluminum silicate; lithium magnesium sodium silicates and hydrated lithium magnesium sodium silicate.

Preferably, the hydrophilic thickener used in the present invention be an organic hydrophilic thickener, and may be selected from natural polymers, modified natural polymers, and synthetic polymers.

It is more preferable that the hydrophilic thickener be selected from natural polymers, modified natural polymers, and a mixture thereof, preferably polysaccharides such as xanthan gum, and cellulose derivatives such as hydroxyethylcellulose, and a mixture thereof.

As the natural polymers and modified natural polymers, mention may be made of organic polymers comprising at least one sugar unit, preferably polysaccharides, for example, guar gums, optionally modified with at least one $C_{1-6}$ hydroxyalkyl group; biopolysaccharide gums of microbial origin, such as scleroglucan gum, xanthan gum; gums derived from plant exudates, such as gum arabic, ghatti gum, acacia senegal gum, karaya gum, gum tragacanth, carrageenan, agar, and carob gum; pectins; alginates such as sodium alginate, potassium alginate, and calcium alginate; starches and derivatives thereof; cellulose derivatives such as methylcellulose, cellulose acetate, hydroxy $(C_{1-6})$ alkylcelluloses, and carboxy $(C_{1-6})$ alkyl celluloses (e.g., carboxymethylcellulose, hydroxymethylcellulose, hydroxyethylcellulose, hydroxypropylcellulose), carboxymethyl hydroxyethyl cellulose, cetyl hydroxyethylcellulose, methyl hydroxypropyl cellulose, and O-(2-hydroxy-3-(trimethylammonio)propyl)hydroxycellulose chloride.

As used herein, the term "sugar unit" means a monosaccharide (i.e., monosaccharide or simple sugar) portion, an oligosaccharide portion (short chains formed from a sequence of monosaccharide units, which may be different), or a polysaccharide portion (long chains consisting of monosaccharide units, which may be different, i.e., polyholosides or polyosides). The saccharide units may also be substituted with at least one substituent selected from alkyl, hydroxyalkyl, alkoxy, acyloxy, and carboxyl substituents, the alkyl radicals comprising from 1 to 4 carbon atoms.

Examples of nonionic, unmodified guar gums include GUARGEL D/15® (Goodrich); VIDOGUM GH 175® (Unipectine), MAYPRO-GUAR 50®, and JAGUAR C® (Meyhall/Rhodia Chimie); and examples of the modified nonionic guar gums include JAGUAR® HP8, HP60, HP120, DC 293 and HP 105 (Meyhall/Rhodia Chimie); and GALACTASOL® 4H4FD2 (Aqualon).

Examples of the biopolysaccharide gums of microbial or plant origin include scleroglucans such as, ACTIGUM® CS from Sanofi Bio Industries; AMIGEL® from Alban Muller International, and also the glyoxal-treated scleroglucans described in French Patent No. 2 633 940; xanthan gums, for example, KELTROL®, KELTROL® T, KELTROL® Tf, KELTROL® Bt, KELTROL® Rd, KELTROL® Cg (Nutrasweet Kelco), RHODICARE® 5, and RHODICARE® H (Rhodia Chimie); starch derivatives, for example, PRIMOGEL® (Avebe); hydroxyethylcelluloses such as CELLOSIZE® QP3L, QP4400H, QP30000H, HEC30000A and Polymer PCG10® (Arnerchol), NATROSOL® 250HHR, 250MR, 250M, 250HHXR, 250HHX, 250HR, HX (Hercules), and TYLOSE® H1000 (Hoechst); hydroxypropylcelluloses, for example, KLUCEL® EF, H, LHF, MF, and G (AquaIon); carboxymethylcelluloses, for example, BLANOSE® 7M8/SF, refined 7M, 7LF, 7MF, 9M31F, 12M31XP, 12M31P, 9M31XF, 7H, 7M31, 7H3SXF (Aqualon), AQUASORB® A500 (Hercules), AMBERGUM® 1221 (Hercules), CELLOGEN® HP810A, HP6HS9 (Montello), and PRIMELLOSE (Avebe).

As the synthetic polymers, mention may be made of polyvinylpyrrolidone, polyacrylic acid, polyacrylamide, non-crosslinked poly(2-acrylamidopropanesulphonic acid) (SIMUGEL® EG from the company SEPPIC), crosslinked poly(2-acrylamido-2-methylpropanulphonic acid), free and partially neutralized with ammonia (HOSTACERIN® AMPS from Clariant), mixtures of non-crosslinked poly(2-acrylamido-2-methylpropane-sulphonic acid) with hydroxyalkylcellulose ethers and with poly(ethylene oxides), as described in U.S. Pat. No. 4,540,510; mixtures of poly ((meth)acrylamide $(C_{1-4})$ alkylsulphonic acid), which may, for example, be crosslinked with a crosslinked copolymer of maleic anhydride and a $C_{1-5}$ alkyl vinyl ether (HOSTACERIN® AMPS/STABILEZE® QM from the company ISF).

It is preferable that the hydrophilic thickener be selected from the group consisting of polysaccharides such as xanthan gum, cellulose derivatives such as hydroxyethylcellulose, acrylate (co)polymers except for the above (i) polymer, and a mixture thereof.

It is also possible to use, as the natural polymers and modified natural polymers, hyaluronic acid and salts thereof, shellac; *Kigelia Africana* fruit extract; *Pyrus Cydonia* seed extract; gellan gum; carrageenan derivatives such as sodium/TEA-undecylenoyl carrageenan, potassium undecylenoyl carrageenan, sodium carrageenan, *Saccharomyces*/carrageenan extract/*Sarcodibtheca gaudichaudii* extract ferment, and hydrolyzed carrageenan; alginic acid derivatives such as algin, propyleneglycol alginate, siloxanetriol alginate, methylsilanol carboxymethyl theophylline alginate, sodium algin sulfate, *Vibrio alginolyticus* ferment filtrate, methylsilanol carboxymethyl theophylline alginate, and hydrolyzed algin; sclerotium gum; steareth-100 mannan and xanthan gum; hyaluronic acid and derivatives thereof such as sodium acetylated hyaluronate, dimethylsilanol hyaluronate, sodium stearoyl hyaluronate, potassium hyaluronate, sodium hyaluronate, propyleneglycol hyaluronate, sodium hyaluronate crosspolymer, dimethylsilanol hyaluronate, hyaluronidase, hydroxypropyl trimonium hyaluronate, hydrolyzed hyaluronic acid, hydrolyzed sodium hyaluronate, and zinc hydrolyzed hyaluronate; pullulan and derivatives thereof such as *Aureobasidium pullunans*/rice bran ferment, *Aureobasdum pullulans* ferment, trimethylsiloxysilylcarbamoyl pullulan, trimethylsilyl pullulan, cholesteryl hexyl dicarbamate pullulan, and myristoyl pullulan; dextrin and derivatives thereof such as dextrin palmitate/ethylhexanoate, amylodextrin, dextrin isostearate, potassium dextrin octenylsuccinate, sodium dextrin octenylsuccinate, TEA-dextrin octenylsuccinate, glyceryl dimaltodextrin, cyclodextrin, dextrin palmitate, hydroxypropyl cyclodextrin, hydroxypropyl trimonium maltodextrin crosspolymer, maltosyl cyclodextrin, maltodextrin, dextrin myristate, methyl cyclodextrin, and cyclodextrin laurate; sodium carboxymethyl dextran; polyglutamic acid; phospholipids; sodium polygamma-glutamate; and sodium polygamma-glutamate crosspolymer.

It is also possible to use, as the acrylate (co)polymers, acrylates/palmeth-25 acrylate copolymer; acrylamide/acryloyldimethyltaurate copolymer; potassium acrylates/$C_{10-30}$ alkyl acrylate crosspolymer; sodium acrylates/$C_{10-30}$ alkyl acrylates crosspolymer;

carbomer and derivatives thereof such as carbomer/papain crosspolymer, calcium potassium carbomer, potassium carbomer, sodium carbomer, TEA-carbomer, carboxyvinylcarbomer, and sodium carboxymethyl starch; AMP-acrylate copolymer; glyceryl acrylate/acrylic acid copolymer; hydroxyethylacrylate/sodium acryloyldimethyl tau rate copolymer; sodium hydroxyethylacrylate/acryloyldimethyl taurate copolymer; styrene/acrylates/ammonium methacrylate copolymer; sodium polyacrylate; sodium polyacrylate starch, polyglyceryl methacrylate, polyacrylate-13, Polyquatemium-10; Polyquaternium-39; and ammonium acryloyldimethyltaurate/VP copolymer. However, it may be preferable not to use sodium polyacrylate starch.

It is also possible to use, as other synthetic polymers, polyvinylalcohol; PEG-800/polyvinylalcohol copolymer; polyvinylalcohol crosspolymer; 2-pyrrolidone/1-ethyl/homopolymer; 1-ethenyl-2-pyrrolidone polymer with acetic acid ethenyl ether; poly(1-ethenyl pyrrolidon-2-one/styrene); polyvinylacetate; polyglycerin-4; PVM/MA copolymer; and ethylene/VA copolymer.

It is more preferable that the hydrophilic thickener be selected from xanthan gum, hydroxyethylcellulose, and ammonium acryloyldimethyltaurate/vinylpyrrolidone copolymer.

It is preferable that the amount of hydrophilic thickener(s) in the composition according to the present invention be 0.01% by weight or more, more preferably 0.1% by weight or more, and even more preferably 0.5% by weight or more, relative to the total weight of the composition.

According to one embodiment of the present invention, the amount of hydrophilic thickener(s) may range from 0.01 to 10% by weight, preferably from 0.1 to 5% by weight, and more preferably from 0.5 to 3% by weight, based on the total weight of the composition according to the present invention.

Pigment

The composition according to the present invention comprises at least one pigment. Two or more pigments may be used in combination. Thus, a single type of pigment or a combination of different types of pigments may be used.

The pigment here means a coloring substance in the form of a particle which is insoluble in liquid such as water and oil at room temperature such as 25° C.

The particle size of the pigment used in the present invention is not limited. It is preferable that the average particle size of the pigment be from 0.1 to 200 µm, more preferably from 1 to 100 µm, and even more preferably from 5 to 50 µm. The term "average particle size" here means a volume-average (median) particle size which can be determined by, for example, the measurement of laser-diffraction/diffusion of the particles.

The pigment used in the present invention can be selected from inorganic pigments, organic pigments, and pearlescent pigments.

As examples, mention may be made, among inorganic pigments, of carbon black (charcoal powder), titanium dioxide (ruble or anatase), optionally surface-treated; black, yellow, red and brown iron oxides, and manganese violet; ultramarine blue, chromium oxide, hydrated chromium oxide, and ferric blue.

It is preferable that the composition according to the present invention includes at least one black pigment, such as carbon black and black iron oxide, in particular carbon black.

For example, mention may be made, among organic pigments, of the pigments D&C Red No. 19, D&C Red No. 9, D&C Red No. 21, D&C Orange No. 4, D&C Orange No. 5, D&C Red No. 27, D&C Red No. 13, D&C Red No. 7, D&C Red No. 6, D&C Yellow No. 5, D&C Red No. 36, D&C Orange No. 10, D&C Yellow No. 6, D&C Red No. 30, D&C Red No. 3, and lakes based on cochineal carmine.

The pearlescent pigments can be selected in particular from white pearlescent pigments, such as mica covered with titanium oxide or bismuth oxychloride, and colored pearlescent pigments, such as titanium oxide-coated mica with iron oxides, titanium oxide-coated mica with ferric blue or chromium oxide, titanium oxide-coated mica with an organic pigment of the above-mentioned type, and pigments based on bismuth oxychloride.

It is preferable that the amount of pigment(s) in the composition according to the present invention be 0.01% by weight or more, more preferably 0.1% by weight or more, and even more preferably 1% by weight or more, relative to the total weight of the composition.

According to one embodiment of the present invention, the amount of pigment(s) may range from 0.01 to 10% by weight, preferably from 0.1 to 5% by weight, and more preferably from 1 to 3% by weight, based on the total weight of the composition according to the present invention.

Water

The composition according to the present invention comprises water.

The pH of the water in the composition according to the present invention is not limited. It is preferable that the pH of the water in the composition according to the present invention be from 5.0 to 11.0, more preferably from 6.0 to 10.0, and even more preferably from 7.0 to 9.0.

According to one embodiment of the present invention, the amount of water may range from 10 to 60% by weight, preferably from 20 to 55% by weight, and more preferably from 30 to 50% by weight, based on the total weight of the composition according to the present invention.

Additional Ingredient(s)

The composition according to the present invention may further comprise at least one additional ingredient. The type of the additional ingredient(s) is not limited, but the composition according to the present invention can typically include surfactant(s) and/or dye(s).

Surfactant

The composition according to the present invention may further comprise at least one surfactant. Two or more surfactants may be used in combination. Thus, a single type of surfactant or a combination of different types of surfactants may be used.

Any surfactant may be used in the composition according to the present invention. The surfactant used in the present invention may be selected from the group consisting of nonionic surfactants, anionic surfactants, cationic surfactants, and amphoteric surfactants. The surfactant may preferably be selected from nonionic surfactants.

Each of the nonionic surfactants, anionic surfactants, cationic surfactants, and amphoteric surfactants which may be used in the composition according to the present invention are described below.

(1) Nonionic Surfactant(s)

According to the present invention, the type of nonionic surfactant is not limited. The nonionic surfactant can, for example, be selected from alcohols, alpha-diols, alkylphenols, and esters of fatty acids that are polyethoxylated, polypropoxylated, or polyglycerolated and have at least one hydrocarbon chain comprising, for example, from 8 to 18 carbon atoms, wherein the number of ethylene oxide or propylene oxide groups may range from 2 to 50, and the number of glycerol groups may range from 2 to 30. The examples of the nonionic surfactant also include copolymers of ethylene oxide and/or of propylene oxide; condensates of ethylene oxide and/or of propylene oxide with higher alcohols; polyethoxylated alkyl amides comprising, for example, from 2 to 30 mol of ethylene oxide; polyglycerolated alkyl amides comprising, for example, from 1 to 5 glycerol groups, such as from 1.5 to 4; ethoxylated fatty acid esters of sorbitan comprising from 2 to 30 mol of ethylene oxide; ethoxylated oils from plant origin; fatty acid esters of sucrose; fatty acid esters of polyethylene glycol; fatty acid mono or diesters of glycerol; ($C_6$-$C_{24}$) alkylpolyglycosides; N—($C_6$-$C_{24}$) alkylglucamine derivatives, amine oxides such as $(C_{10}\text{-}C_{14})$ alkylamine oxides or $N\text{—}(C_{10}\text{-}C_{14})$ acylaminopropylmorpholine oxides; and mixtures thereof.

The nonionic surfactant may preferably be selected from mono-oxyalkylenated or poly-oxyalkylenated, mono-glycerolated or poly-glycerolated nonionic surfactants. The oxyalkylene units therein are preferably oxyethylene or oxypropylene units, or a combination thereof, and more preferably oxyethylene units. For example, beheneth-30, polyglyceryl-10 stearate, and/or polyglyceryl-10 myristate can preferably be used as the nonionic surfactant(s).

(2) Anionic Surfactant(s)

According to the present invention, the type of anionic surfactant is not limited. The anionic surfactant can, for example, be selected from the group consisting of alkyl sulfates; alkyl ether sulfates; alkylamido ether sulfates; alkylaryl polyether sulfates; monoglyceride sulfates; alkylsulfonates; alkylphosphates; alkylamide sulfonates; alkylaryl sulfonates; α-olefin sulfonates; paraffin sulfonates; alkyl sulfosuccinates; alkyl ether sulfosuccinates; alkylamide sulfosuccinates; alkyl sulfoacetates; alkyletherphosphates; acyl sarcosinates; acyl glutamates; alkylpolyglycoside carboxylic ethers; alkylpolyglycoside sulfosuccinates; alkyl sulfosuccinamates; acyl isethionates; N-acyl taurates; fatty acid salts; coconut oil add salts or hydrogenated coconut oil acid salts; acyl lactylates; alkyl-D-galactoside uronic acid salts; polyoxyalkylenated alkyl ether carboxylic acid salts; polyoxyalkylenated alkylaryl ether carboxylic acid salts; and polyoxyalkylenated alkylamido ether carboxylic acid salts, wherein the alkyl group therein can have 6 to 30 carbon atoms, and preferably 12 to 20 carbon atoms.

It may be preferable that the anionic surfactant be selected from salts of $(C_6\text{-}C_{30})$ alkyl sulfate or polyoxyalkylenated $(C_6\text{-}C_{30})$ alkyl ether carboxylic acid salts.

In at least one embodiment, the anionic surfactants are in the form of salts such as salts of alkali metals, for instance, sodium; salts of alkaline-earth metals, for instance, magnesium; ammonium salts; amine salts; and amino alcohol salts.

(3) Cationic Surfactant(s)

According to the present invention, the type of cationic surfactant is not limited. The cationic surfactant may be selected from the group consisting of optionally polyoxyalkylenated, primary, secondary, or tertiary fatty amine salts, quaternary ammonium salts, and mixtures thereof. The cationic surfactants can, for example, be selected from quaternary ammonium salts of general formula (I) below:

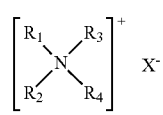

wherein $R_1$, $R_2$, $R_3$, and $R_4$, which may be identical or different, are selected from linear and branched hydrocarbon groups comprising from 1 to 30 carbon atoms and optionally comprising heteroatoms such as oxygen, nitrogen, sulfur, and halogens. The hydrocarbon groups may be selected, for example, from aliphatic hydrocarbon groups such as alkyl, alkoxy, $C_2\text{-}C_6$ polyoxyalkylene, alkylamide, $(C_{12}\text{-}C_{22})$ alkylamido $(C_2\text{-}C_6)$ alkyl, $(C_{12}\text{-}C_{22})$ alkylacetate, and hydroxyalkyl groups; and aromatic groups such as aryl and alkylaryl; and $X^-$ is selected from halides, phosphates, acetates, lactates, $(C_2\text{-}C_6)$ alkyl sulfates, and alkyl- or alkylarylsulfonates; and quaternary ammonium salts of imidazoline, for instance, those of formula (II) below:

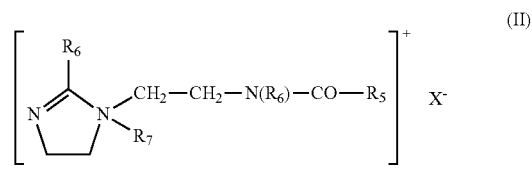

wherein:

$R_5$ is selected from alkenyl and alkyl groups comprising from 8 to 30 carbon atoms, for example, fatty acid derivatives of tallow or of coconut;

$R_6$ is selected from hydrogen, $C_1\text{-}C_6$ alkyl groups, and alkenyl and alkyl groups comprising from 8 to 30 carbon atoms;

$R_7$ is selected from $C_1\text{-}C_6$ alkyl groups;

$R_8$ is selected from hydrogen and $C_1\text{-}C_6$ alkyl groups; and $X^-$ is selected from halides, phosphates, acetates, lactates, alkyl sulfates, alkyl sulfonates, and alkylaryl sulfonates ($R_5$ and $R_6$ may be, for example, a mixture of groups selected from alkenyl and alkyl groups comprising from 12 to 21 carbon atoms, such as fatty acid derivatives of tallow, $R_7$ is methyl, and $R_8$ is hydrogen).

The cationic surfactants can, for example, also be selected from diquaternary ammonium salts of formula (III):

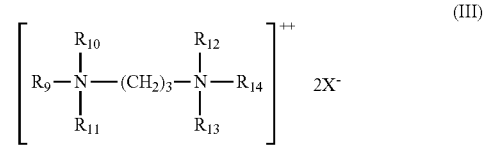

wherein:

$R_9$ is selected from aliphatic groups comprising from 16 to 30 carbon atoms;

$R_{10}$ is selected from hydrogen or alkyl groups comprising from 1 to 4 carbon atoms or a group $(R_{16a})(R_{17a})(R_{18a})N^+(CH_2)_3$;

$R_{11}$, $R_{12}$, $R_{13}$, $R_{14}$, $R_{16a}$, $R_{17a}$, and $R_{18a}$, which may be identical or different, are selected from hydrogen and alkyl groups comprising from 1 to 4 carbon atoms; and $X^-$ is selected from halides, acetates, phosphates, nitrates, ethyl sulfates, and methyl sulfates.

(4) Amphoteric Surfactant(s)

According to the present invention, the type of amphoteric surfactant is not limited. The amphoteric or zwitterionic surfactants can, for example, be amine derivatives such as aliphatic secondary or tertiary amines, and optionally quaternized amine derivatives, in which the aliphatic group is a linear or branched chain comprising 8 to 22 carbon atoms and containing at least one water-solubilizing anionic group (for example, carboxylate, sulphonate, sulphate, phosphate or phosphonate).

The amphoteric surfactant may preferably be selected from the group consisting of betaines and amidoaminecarboxylated derivatives.

The betaine-type amphoteric surfactant is preferably selected from the group consisting of alkylbetaines, alkylamidoalkylbetaines, sulfobetaines, phosphobetaines, and alkylamidoalkylsulfobetaines, in particular, $(C_8\text{-}C_{24})$ alkylbetaines, $(C_8\text{-}C_{24})$ alkylamido $(C_1\text{-}C_8)$ alkylbetaines, sulphobetaines, and $(C_8\text{-}C_{24})$ alkylamido $(C_1\text{-}C_8)$ alkyisulphobetaines. In one embodiment, the amphoteric surfactants of betaine type are selected from $(C_8\text{-}C_{24})$ alkylbetaines, $(C_8\text{-}$ $C_{24}$) alkylamido ($C_1$-$C_8$) alkylsulphobetaines, sulphobetaines, and phosphobetaines.

According to one embodiment of the present invention, the amount of surfactant(s), if present, in the composition according to the present invention may range from 0.001 to 10% by weight, preferably from 0.01 to 5% by weight, and more preferably from 0.1 to 1% by weight, based on the total weight of the composition according to the present invention.

Alternatively, the composition according to the present invention may include surfactant(s) in an amount of less than 0.1% by weight, preferably less than 0.01% by weight, and more preferably less than 0.01% by weight, based on the total weight of the composition according to the present invention. In this case, it is most preferable that the composition according to the present invention include no surfactant(s).

Dye

The composition according to the present invention may further comprise at least one dye. Two or more dyes may be used in combination. Thus, a single type of dye or a combination of different types of dyes may be used.

The dye here means a coloring substance which is soluble in liquid such as water and oil at room temperature such as 25° C.

The dyes can be selected from, for example, Sudan red, D&C Red No 17, D&C Green No 6, β-carotene, soybean oil, Sudan brown, D&C Yellow No 11, D&C Violet No 2, D&C Orange No 5, quinoline yellow, annatto, and bromo acids.

It is preferable that the amount of dye(s), if present, in the composition according to the present invention be 0.01% by weight or more, more preferably 0.1% by weight or more, and even more preferably 1% by weight or more, relative to the total weight of the composition.

According to one embodiment of the present invention, the amount of dye(s), if present, may range from 0.01 to 10% by weight, preferably from 0.1 to 5% by weight, and more preferably from 1 to 3% by weight, based on the total weight of the composition according to the present invention.

Other Optional Ingredients

The composition according to the present invention may further comprise at least one other additional ingredient such as an aqueous organic solvent.

The aqueous organic solvent may be selected from, for example, $C_1$-$C_4$ alcohols, such as ethanol and isopropanol; polyols and polyol ethers such as glycerol, 2-butoxyethanol, propyleneglycol, butyleneglycol, monomethyl ether of propylene glycol, monoethyl ether and monomethyl ether of diethylene glycol; and aromatic alcohols such as benzyl alcohol and phenoxyethanol; analogous products; and mixtures thereof.

The aqueous organic solvent(s) may be present in an amount ranging from 0.001 to 10% by weight, preferably from 0.01 to 5% by weight, and more preferably from 0.1 to 3% by weight, based on the total weight of the composition.

Since the composition according to the present invention is applied on the skin, in particular, the eyelids, the composition may include ingredients typically employed in cosmetics, specifically, acids, bases, salts, antioxidants, UV absorbing agents, whitening agents, blood circulation accelerators, metal chelators, sebum controllers, powders except for pigments, astringents, skin softeners, oils, silicones, silicone derivatives, natural extracts derived from animals or vegetables, waxes, preservatives, and the like within a range which does not impair the effects of the present invention.

The composition according to the present invention can be prepared by mixing the above essential ingredients (i) to (iv), as well as the above additional or optional ingredient(s), by using a conventional mixer such as a ball mill and a homogenizer. The mode of mixing ingredients is not limited, and therefore, the essential ingredients (i) to (iv) can be mixed simultaneously by, for example, adding the ingredients (i) to (iii) together to the ingredient (iv), or sequentially by, for example, the ingredient (i) being firstly added to the ingredient (iv), the ingredient (ii) being secondly added to the ingredient (iv), and then, the ingredient (iii) being added to the ingredient (iv).

It is preferable that the composition according to the present invention be packaged into a tube, such that it is allowed to dispense the composition according to the present invention in the form of a thin line.

The composition according to the present invention can be used for making up eyes, in particular eyelids, and therefore, the composition according to the present invention is a cosmetic composition, preferably a colored cosmetic composition, and more preferably a colored eye-makeup cosmetic composition.

Cosmetic Use and Process

Next, the use of the composition according to the present invention and the cosmetic process using the composition according to the present invention will be described below in a detailed manner.

The composition according to the present invention can be used, as it is, for making up eyes, in particular eyelids, and preferably the edges of the eyelids. Thus, the composition according to the present invention can be used as, for example, an eyeliner.

The composition according to the present invention can also be used for making up eyes, in particular eyelids, and preferably the edges of the eyelids, by adhering fake eyelashes to the eyelids, and preferably the edges of the eyelids. Thus, the composition according to the present invention can also be used as, for example, an adhesive for fake eyelashes.

The fake eyelash herein means an artificial cosmetic device which has been conventionally used in the art for cosmetic processing for the eyes, which comprises a base which is typically in the form of a linear body, and a plurality of fibers wherein one end of the fibers is fixed on the base.

The composition according to the present invention can be used as a cosmetic product which functions as both an eyeliner and an adhesive for fake eyelashes. In this case, the composition according to the present invention can be used as an "eye glue liner". Due to the double cosmetic effects by the color lines at the edges of the eyelids and by the fake eyelashes, for example, the composition according to the present invention as an "eye glue liner" can provide superior eye makeup effects.

Thus, another embodiment of the present invention is the use of a colored cosmetic composition comprising:
 (i) at least one polymer which has a Tg of −30° C. or less;
 (ii) at least one hydrophilic thickener;
 (iii) at least one pigment; and
 (iv) water,
for making up eyes, in particular eyelids, preferably the edges of the eyelids, as an eyeliner and/or an adhesive for fake eyelashes.

The polymer, the hydrophilic thickener, the pigment, and the water, as well as the additional or optional ingredients in the composition in this embodiment are as explained above.

The present invention also relates to a cosmetic process or method for making up eyes.

The cosmetic process according to the present invention comprises:
(1) applying the colored cosmetic composition according to the present invention to eyelids; and
(2) adhering fake eyelashes to the eyelids, preferably the edges of the eyelids, or
(1) applying the colored cosmetic composition according to the present invention to fake eyelashes; and
(2) adhering the fake eyelashes to eyelids, preferably the edges of the eyelids.

The composition according to the present invention in this embodiment is as explained above.

It goes without saying that, in the cosmetic process according to the present invention, the fake eyelashes are adhered to the eyelids to which the composition according to the present invention has been applied, and that a part of the fake eyelashes to which the composition according to the present invention has been applied is adhered to eyelids.

The use and process according to the present invention can provide a good feeling to use, and can provide appropriate adhesives to eyelids and/or fake eyelashes such that the use and process according to the present invention can provide eye makeup effects for a long period of time and/or can fix the fake eyelashes on the eyelids, in particular, the edges of the eyelids, for a long period of time, while the eye-makeup and/or fake eyelashes can be removed, when necessary to be removed, with a comfortable feeling of removal from the eyelids, in particular, the edges of the eyelids.

The removed fake eyelashes can be re-attached to eyelids, in particular the edges of the eyelids, because the composition according to the present invention applied onto fake eyelashes or eyelids, in particular the edges of the eyelids, has sufficient adhesiveness.

The present invention may also relate to fake eyelashes to which the composition according to the present invention has been applied.

In this embodiment, the composition according to the present invention may preferably be applied to each of the bases of fake eyelashes such that the base can be attached to an eyelid, in particular, the edge of the eyelid, of a user.

Since the composition according to the present invention has appropriate adhesiveness, the fake eyelashes according to the present invention can stay on eyelids, in particular, the edges of the eyelids, for a long period of time, while they can be removed without an uncomfortable feeling during use. In addition, the detached fake eyelashes still have sufficient adhesiveness so that they can be re-attached to the eyelids, in particular the edges of the eyelids.

EXAMPLES

The present invention will be described in a more detailed manner by way of examples. However, they should not be construed as limiting the scope of the present invention.

Examples 1-8 and Comparative Examples 1 and 2

The following eye-makeup compositions shown in Tables 1-3 were prepared by mixing the ingredients shown in Tables 1-3. In Tables 1-3, the values are based on % by weight, relative to the total weight of the composition.

TABLE 1

|  | Example 1 | Example 2 | Example 3 | Comparative Example 1 |
| --- | --- | --- | --- | --- |
| Acrylates/Ethylhexylacrylate Copolymer* | 46.75 | 46.75 | 46.75 | 46.75 |
| Charcoal Powder | 2.5 | 2.5 | 2.5 | 2.5 |
| Hydroxyethylcellulose | 0.5 | 0.3 | 0.1 | — |
| 1,3-Butyleneglycol | 1.0 | 1.0 | 1.0 | 1.0 |
| Glycerin | 2.0 | — | — | 2.0 |
| Phenoxyethanol | 0.9 | 0.9 | 0.9 | 0.9 |
| Sodium Dehydroacetate | 0.475 | 0.475 | 0.475 | 0.475 |
| Polyglyceryl-10 Stearate | 0.4 | 0.4 | 0.4 | 0.4 |
| Polyglyceryl-10 Myristate | 0.4 | 0.4 | 0.4 | 0.4 |
| Citric Add | 0.05 | 0.05 | 0.05 | 0.05 |
| Sodium Hyaluronate | 0.001 | 0.001 | 0.001 | 0.001 |
| Water | 45.024 | 47.224 | 47.424 | 45.524 |
| Total (wt %) | 100 | 100 | 100 | 100 |

TABLE 2

|  | Example 4 | Example 5 |
| --- | --- | --- |
| Acrylates/Ethylhexylacrylate Copolymer* | 46.75 | 46.75 |
| Charcoal Powder | 2.5 | 2.5 |
| Ammonium Acryloyldimethyltaurate/VP copolymer | 0.5 | — |
| Xanthan Gum | — | 0.5 |
| 1,3-Butyleneglycol | 1.0 | 1.0 |
| Glycerin | 2.0 | 2.0 |
| Phenoxyethanol | 0.9 | 0.9 |
| Sodium Dehydroacetate | 0.475 | 0.475 |
| Polyglyceryl-10 Stearate | 0.4 | 0.4 |
| Polyglyceryl-10 Myristate | 0.4 | 0.4 |
| Citric Acid | 0.05 | 0.05 |
| Sodium Hyaluronate | 0.001 | 0.001 |
| Water | 45.024 | 45.024 |
| Total (wt %) | 100 | 100 |

TABLE 3

|  | Example 6 | Example 7 | Example 8 | Comparative Example 2 |
| --- | --- | --- | --- | --- |
| Acrylates/Ethylhexylacrylate Copolymer* | 46.75 | 46.75 | 46.75 | 46.75 |
| Charcoal Powder | 2.5 | 2.5 | 2.5 | 2.5 |
| Hydroxyethylcellulose | — | 0.3 | 0.2 | — |
| Ammonium Acryloyldimethyltaurate/VP copolymer | 0.25 | 0.2 | — | — |
| Xanthan Gum | 0.25 | — | — | — |
| Beheneth-30 | — | — | 1.0 | 1.0 |
| 1,3-Butyleneglycol | 1.0 | 1.0 | 1.0 | 1.0 |
| Glycerin | 2.0 | 2.0 | 1.0 | 2.0 |
| Phenoxyethanol | 0.9 | 0.9 | 0.9 | 0.9 |
| Sodium Dehydroacetate | 0.475 | 0.475 | 0.475 | 0.475 |
| Polyglyceryl-10 Stearate | 0.4 | 0.4 | 0.4 | 0.4 |
| Polyglyceryl-10 Myristate | 0.4 | 0.4 | 0.4 | 0.4 |

TABLE 3-continued

|  | Example 6 | Example 7 | Example 8 | Comparative Example 2 |
|---|---|---|---|---|
| Citric Acid | 0.05 | 0.05 | 0.05 | 0.05 |
| Sodium Hyaluronate | 0.001 | 0.001 | 0.001 | 0.001 |
| Water | 45.024 | 45.024 | 45.324 | 44.524 |
| Total (wt %) | 100 | 100 | 100 | 100 |

*Polymer ingredient in DAITOSOL ® 5500GM marketed by DAITO KASEI KOGYO Co., Ltd.

Stability Evaluation

Each of the compositions according to Examples 1-8 and Comparative Examples 1 and 2 was charged into a transparent container, and stored at room temperature or 50° C. for 1 month. The appearance of the composition was evaluated by visual observation in accordance with the following criteria.

+++: No phase separation or no white line caused by the separation of the copolymer was observed at room temperature and 50° C. after 1 month ++: No phase separation or no white line was observed at room temperature after 1 month, but slight or clear phase separation or white line was observed at 50° C. after 1 month +: Clear or slight phase separation or white line was observed at room temperature and 50° C. after 1 month The results of the evaluation are shown in Tables 4-6 below.

TABLE 4

|  | Example 1 | Example 2 | Example 3 | Comparative Example 1 |
|---|---|---|---|---|
| Stability Evaluation | +++ | ++ | ++ | + |

TABLE 5

|  | Example 4 | Example 5 |
|---|---|---|
| Stability Evaluation | ++ | +++ |

TABLE 6

|  | Example 6 | Example 7 | Example 8 | Comparative Example 2 |
|---|---|---|---|---|
| Stability Evaluation | +++ | +++ | ++ | + |

Sensory Evaluation

Each of the compositions according to Examples 1-8 is applied, as an eyeliner, to the edges of eyelids of each of 10 panelists in total. The feeling to use of the compositions according to Examples 1-8 is good.

The adhesiveness of the compositions according to Examples 1-8 to the eyelids is sufficient to provide long term eye-makeup effects, while they can be removed by cleansing oil.

Next, each of the compositions according to Examples 1-8 is applied to a fake eyelash. After drying the applied composition, the fake eyelash is attached to the eyelid of each of 10 panelists in total.

As controls, a commercial adhesive product (Main Ingredient: Acrylic Resin, Control 1) for fake eyelashes comprising 54% by weight of acrylic resin and 46% by weight water is applied to a fake eyelash. After drying the applied composition, the fake eyelash is attached to the other eyelid of each of the 5 panelists. In addition, instead of Control 1, another commercial adhesive product (Main Ingredient: Natural Gum, Control 2) for fake eyelashes comprising natural gum latex is applied to a fake eyelash. After drying the applied composition, the fake eyelash is attached to the other eyelid of each of the 5 panelists.

The removability of the fake eyelash and irritation caused by the fake eyelash are compared for the 10 panelists in total.

The results are that the compositions according to Examples 1-8 show better removability than Control 1, with a comfortable feeling when removing the fake eyelash, and that the compositions according to Examples 1-8 show better removability than Control 2, and are less irritative than Control 2.

The invention claimed is:

1. A liquid colored adhesive cosmetic composition for adhering fake eyelashes on eyelids, comprising:
    (i) an adhesive polymer consisting of at least one acrylate copolymer having a Tg of −30 ° C. or less present in an amount of from 10% by weight to 70% by weight relative to the total weight of the composition wherein the at least one acrylate copolymer in (i) is formed by at least one monomer selected from the group consisting of $C_{1-6}$ alkyl (meth)acrylates, $C_{1-6}$ hydroxyalkyl (meth)acrylates, $C_{1-6}$ alkoxy $C_{1-6}$ alkyl (meth)acrylates, polyoxyalkene (meth)acrylates, $C_{1-6}$ alkylpolyoxyalkylene (meth)acrylates, $C_{8-22}$ alkyl (meth)acrylates, and a mixture thereof;
    (ii) at least one hydrophilic thickener present in an amount of from 0.01% by weight to 10% by weight relative to the total weight of the composition;
    (iii) at least one pigment;
    (iv) water present in an amount of from 10% by weight to 60% by weight relative to the total weight of the composition; and
    (v) at least one aqueous organic solvent present in an amount of from 0.001% by weight to 5% by weight relative to the total weight of the composition.

2. The liquid colored adhesive cosmetic composition according to claim 1, wherein the at least one acrylate copolymer in (i) is in the form of particles.

3. The liquid colored adhesive cosmetic composition according to claim 2, wherein the average particle size of the at least one acrylate copolymer in (i) is from 100 to 300 nm.

4. The liquid colored adhesive cosmetic composition according to claim 2, wherein the particles of the at least one acrylate copolymer in (i) are dispersed in the water in (iv).

5. The liquid colored adhesive cosmetic composition according to claim 1, wherein the Tg of the at least one acrylate copolymer in (i) is −60° C. or less.

6. The liquid colored adhesive cosmetic composition according to claim 1, wherein the at least one acrylate copolymer in (i) is selected from the group consisting of acrylates/ethylhexyl acrylate copolymers and styrene/acrylates copolymers.

7. The liquid colored adhesive cosmetic composition according to claim 1, wherein the amount of the at least one acrylate liquid colored adhesive cosmetic copolymer in (i) is 20% by weight, relative to the total weight of the composition.

8. The at least one acrylic liquid colored adhesive cosmetic composition according to claim 1, wherein the aqueous organic solvent is selected from ethanol, isopropanol; glycerol, 2-butoxyethanol, propyleneglycol, butyleneglycol, monomethyl ether of propylene glycol, monoether ether and monomethyl ether of diethylene glycol; benzyl alcohol and phenoxyethanol.

9. The liquid colored adhesive cosmetic composition according to claim 1, wherein the aqueous organic solvent is ethanol or phenoxyethanol.

10. The liquid colored adhesive cosmetic composition according to claim 1, wherein the hydrophilic thickener is xanthan gum or hydroxyethylcellulose.

11. The liquid colored adhesive cosmetic composition according to claim 1, wherein the average particle size of the pigment is from 0.1 to 200 µm.

12. The liquid colored adhesive cosmetic composition according to claim 1, wherein the pigment comprises one or more of black, yellow, red or brown iron oxide.

13. The liquid colored adhesive cosmetic composition according to claim 1, wherein the at least one acrylate copolymer is present in an amount of from 30% by weight to 70% by weight relative to the total weight of the liquid colored adhesive cosmetic composition.

14. A cosmetic process for making up eyes and for adhering a fake eyelash on an eyelid, comprising:
(1) applying the liquid colored adhesive cosmetic composition according to claim 1 to an eyelid; and
(2) adhering a fake eyelash to the eyelid.

15. A cosmetic process for making up eyes and for adhering a fake eyelash on an eyelid, comprising:
(1) applying the liquid colored adhesive cosmetic composition according to claim 1 to a fake eyelash; and
(2) adhering the fake eyelash to an eyelid.

* * * * *